United States Patent [19]
du Manoir et al.

[11] Patent Number: 5,179,021
[45] Date of Patent: Jan. 12, 1993

[54] PULP BLEACHING PROCESS COMPRISING OXYGEN DELIGNIFICATION AND XYLANASE ENZYME TREATMENT

[75] Inventors: John R. du Manoir, Oakville; Paul Dubelsten, Mississauga, both of Canada

[73] Assignee: GIL Inc. (now ICI Canada Inc.), North York, Canada

[21] Appl. No.: 308,529

[22] Filed: Feb. 10, 1989

[51] Int. Cl.⁵ ............................................. D21C 3/00
[52] U.S. Cl. .................................... 435/278; 162/63; 162/65
[58] Field of Search ........................................ 435/278

[56] References Cited

U.S. PATENT DOCUMENTS 4,687,745  8/1987  Farrell ................................... 435/278
4,923,565  5/1990  Fuentes et al. ........................ 435/278

FOREIGN PATENT DOCUMENTS 2557894  7/1985  France .

OTHER PUBLICATIONS

Chauvet, J. M., Comtat, J. and Noe, P.; International Symposium on Wood & Pulping Chemistry Proceedings, Paris, p. 325 (1987).

Viikari, L., Rauna, M., Kantelinen, A., Linko, M. and Sundquist, J.; International Symposium on Wood & Pulping Chemistry, Paris (1987).

Paice, M. G., Bernier, R., Jurasek, L.; Biotech. and Bioeng., 32, pp. 235-239 (1988).

*Primary Examiner*—Sam Rosen
*Attorney, Agent, or Firm*—C. Brian Barlow

[57] ABSTRACT

Process for bleaching lignocellulosic material comprising an oxygen bleaching treatment and an enzymatic treatment with a substantially cellulase-free xylanase, which process is compatible with, and can be incorporated into, conventional bleaching sequences. The process provides a delignified and bleached pulp using lower amounts of chlorine-containing compounds, and the opportunity of eliminating the use of elemental chlorine, thereby reducing the polluting effluent from a pulp mill employing the process. Also, a greater extent of delignification can be achieved while retaining acceptable pulp strength properties. The oxygen bleaching treatment and the enzymatic treatment are done in series.

17 Claims, No Drawings

PULP BLEACHING PROCESS COMPRISING OXYGEN DELIGNIFICATION AND XYLANASE ENZYME TREATMENT

The present invention relates to a process for the bleaching of lignocellulosic material employing an oxygen treatment and an enzymatic treatment with xylanase.

Lignocellulosic material in fibrous form is in wide commercial use as a raw material for the manufacture of paper, cardboard, construction board, etc. The raw material is usually wood whose principle components are cellulose, and a three-dimensional macromolecule—lignin, which is considered to be embedded in a matrix of cellulosic and hemicellulosic polysaccharides. It is generally accepted that the bonding that exists between the different components are established through linkages of different chemical nature. For instance, blocks of lignin are thought of as being associated through hemicellulose chains, the hemicellulose being another component of lignocellulosic material. In hardwoods, the predominant hemicellulose is glucuronoxylan, which includes a polymer of D-xylose, and hereinafter referred to as xylan.

In order to produce strong and bleachable papermaking fibres, the lignocellulosic material must be treated to remove lignin, and normally, the initial part of this treatment takes place in a digester in the presence of chemicals such as sodium hydroxide and sodium sulphide (to produce a kraft pulp) or sulphites, usually sodium or magnesium, (to produce a sulphite pulp), thus producing chemical pulps. The removal of lignin is referred to as delignification. The lignin content of wood pulps is measured by a permanganate oxidation test according to a Standard Method of the Technical Association Of The Pulp And Paper Industry (TAPPI), and is reported as a Kappa Number. The chemical pulp from the digester still contains an appreciable amount of residual lignin at this stage, and in some cases is suitable for making construction or packaging paper without further purification. For most applications, such as the manufacture of printing, writing and sanitary papers, however, the pulp is too dark in colour and must be brightened by bleaching. It is at this point, that the process of the present invention may be employed, i.e., in the process of bleaching lignocellulosic material, said material referred to hereinbefore as chemical pulp. The initial stages of bleaching also result in further delignification.

The conventional method for further delignifying and bleaching pulp has been to employ a variety of multi-stage bleaching sequences, including anywhere from three to six stages, or steps, and with or without washing between steps. The objective in bleaching is to provide a pulp, in the case of chemical pulps, of sufficiently high brightness and strength for the manufacture of paper and tissue products. Characteristically, pulps of brightness 85% to 90% ISO are produced. Pulps of higher brightness can be produced from certain unbleached pulp types but at higher cost and at the risk or expense of pulp strength quality losses. The asymptotic limit of brightness that is encountered for a given pulp type in conventional bleaching processes is referred to herein as the brightness ceiling. This brightness ceiling is the brightness level, over which brightness the process of further bleaching would be considered too detrimental to the quality of the pulp, prohibitively uneconomical, or unachievable for certain materials.

Traditionally, the bleaching sequences have been based on the use of chlorine and chlorine-containing compounds, in one form or another. Some of the chlorine-containing compounds that are used are chlorine, denoted C, chlorine dioxide, denoted D, and hypochlorites, denoted H, usually sodium hypochlorite. Chlorine, with or without admixture of chlorine dioxide, is commonly employed to initiate the bleaching of chemical pulp, followed by extraction of the chlorine-treated pulp in an aqueous alkaline medium, together denoted C-E. The chlorine charge (or chlorine plus chlorine dioxide charge, the chlorine dioxide expressed on a chlorine oxidizing equivalent basis) in the C stage is proportional to the lignin content (Kappa Number) of the pulp being treated. The alkaline extraction stage is used to solubilize and remove a major portion of the chlorinated and oxidized residual lignin, and also some hemicellulose is removed.

With the advent of stricter environmental regulations designed to abate water and air pollution problems associated with chlorine-containing bleaching chemicals, coupled with the extensive recovery systems needed for the removal of chlorine-containing waste products, there is a distinct advantage in the reduction and preferably the avoidance of such chemicals in bleaching processes. Furthermore, if chlorine-containing waste is recycled through a kraft process black liquor recovery system, damage to the evaporator and furnace will result. A build-up of sodium chloride would also occur, causing damage to the furnace. Therefore, the pulp and paper industry has directed its attention to other bleaching chemicals which might avoid these problems.

One of the significant advancements in the industry in the past two decades has been associated with the use of oxygen as a delignifying and bleaching agent. One application is the use of oxygen in conjunction with a conventional alkaline extraction stage, denoted Eo, following a chlorination. The alkaline extraction stage following the chlorination stage may contain other oxidative agents, such as peroxide (p) or hypochlorite (h) in combination with or in place of the oxygen. Such stages are accordingly denoted Epo, Eho, Ep or Eh, and each referred to generally as an oxidative extraction.

The other main application of oxygen is for, primarily, delignification following the pulping digester and preceding bleaching and denoted O. Oxygen used in this fashion is applied to an unbleached pulp in alkaline medium under pressure. While the use of oxygen has provided alternative methods for delignification and bleaching, it is only of limited usefulness since it adversely affects the degree of polymerization of the cellulose, which is considered a drawback. The degree of polymerization of the cellulose is an indication of pulp strength and is measured as pulp viscosity by a TAPPI Standard Method. One criterion necessary for a bleaching stage is that the resultant pulp viscosity must not be substantially decreased. Generally, it is observed that only approximately up to 50% of the lignin remaining after pulping can be removed in this step with a pulp viscosity loss that is tolerable. Attempts at greater extents of delignification in this step are at the expense of further viscosity losses. The presence of magnesium ion in this step is known to assist in minimizing these viscosity losses. The pulp viscosity losses are believed to arise from the chemical modification (degradation) of the cellulose and hemicellulose portions.

Applications employing oxygen delignification have contributed to a reduction in the use of chlorine-containing compounds in bleaching sequences since the chemical charge in the chlorination stage is based upon the pulp lignin content, and this lignin content is reduced substantially (about 40% to 50%) by oxygen delignification.

Enzymes have been studied for their use in the treatment of lignocellulosic material. For example, ligninolytic enzymes, particularly from white-rot fungi, have been shown to degrade lignin to varying degrees. Also, cellulase enzymes are well known to degrade cellulose and are of commercial interest in the food industry and in the manufacture of alcohols. In the manufacture of pulp for the purpose of paper-making, the effect of a cellulase enzyme would be detrimental owing to the resulting decrease in the degree of polymerization of the cellulose that would occur.

In view of the hemicellulose component of lignocellulosic material, there have been studies reported on the effects of a xylanase enzyme on wood pulps. The xylanase expectedly selectively reacts with the xylan of the hemicellulose.

French Patent Application No. 2,557,894 (published 1985) discloses a process for treating a hardwood bleached kraft or a softwood bleached sulphite chemical pulp with an enzyme solution containing xylanase to reduce the amount of subsequent beating or refining required for papermaking. Particularly large amounts of enzyme were required for the treatment of the bleached pulp in order to impart the desired effect. Further, the xylanase secreted by the basidiomycete mushroom *Sporotrichum dimorphosporum* for use in the reduction of refining, was not cellulose-free and the detrimental cellulose activity was suppressed by the addition of mercuric chloride to the process. Owing to the known toxic and other harmful effects associated with exposure to mercury-containing compounds, their use is not acceptable.

Chauver et al. (Proceedings of The International Symposium On Wood And Pulping Chemistry, Paris, p. 325, 1987) reported on the use of a xylanase preparation obtained from the basidomycete mushroom *Sporotrichum dimorphosporum* for use as a pretreatment for a conventional chemical pulp bleaching sequence, C/D-E-D-E-D. The crude enzyme complex is treated with mercuric chloride to inactivate all polysaccharidase, except xylanase, activities. The pulp pretreatment comprises an enzymatic treatment followed by washing and subsequent aqueous acid soaking that results in up to a 14% Kappa number reduction for the hardwood sample. The pulp strength is not modified.

The application of xylanase on hardwood and softwood kraft pulp for the purpose of brightness improvement and improved Kappa number reduction upon subsequent chemical treatment with hydrogen peroxide or in a bleaching sequence is discussed by Viikari et al. (Proceedings of The International Symposium On Wood and Pulping Chemistry, Paris, 1987). The xylanases are obtained by fermentation of a strain of fungus of the species *Aspergillis awamori* or by fermentation of bacterial strains of *Streptomyces olivochromogenes* or *Bacillus subtilis*. The xylanases exhibit both xylanase and xylosidase activities, except the xylanase from the latter bacterium which is xylosidase-free. The enzyme preparations contain traces of cellulase activity. A small brightness increase of 1.0 to 3.4 brightness points is observed with either the hardwood or softwood pulp after a hydrogen peroxide treatment following the enzymatic treatment. In many instances, the resulting pulp viscosities were preserved or only slightly lower. There is no indication as to the effect of the enzyme treatment alone on the pulp properties.

Paice et al. (Biotech. and Bioeng., Vol. 32, p. 235-239, 1988) disclose a treatment of an unbleached hardwood pulp by a sequential xylanase treatment followed by a treatment with 1% on pulp sodium hydroxide. This two-step process provided a brightness increase and reduction in Kappa Number. Also, some, but not all of the brightness enhancement is retained after subsequent C-E-D bleaching. The xylanase was reportedly cellulase-free and produced by an *E. coli* clone.

Surprisingly, we have now found that chemical pulp can be more effectively delignified and bleached in sequences including an oxygen delignification step and a xylanase treatment.

Therefore, it is an object of the present invention to provide a process for increasing the extent of delignification of lignocellulosic material without incurring significant additional viscosity loss.

It is a further object of the present invention to provide a process for the bleaching of lignocellulosic material using lower amounts of chlorine-containing bleaching agents than are conventionally employed, or essentially eliminating the use of elemental chlorine, thus providing a more environmentally acceptable process.

It is yet a further object of the present invention to provide a process for the delignification and bleaching of lignocellulosic material that effectively raises the brightness ceiling of said material.

Accordingly, in one aspect of the present invention there is provided a process for the bleaching of lignocellulosic material having xylanase hydrolyzable xylosidic linkages, said process comprising treating said lignocellulosic material with (a) oxygen or an oxygen-containing gas in an alkaline medium, and (b) a sufficient amount of substantially cellulase-free xylanase to effect the hydrolysis of said hydrolyzable xylosidic linkages in said material;

to provide a bleached lignocellulosic material.

In the process according to the present invention, the treatment with xylanase may precede the treatment with oxygen or an oxygen-containing gas. In the generally preferred embodiment of the process according to the present invention the treatment with oxygen or an oxygen-containing gas precedes the treatment with xylanase.

The treatment of the lignocellulosic material with oxygen or an oxygen-containing gas is carried out on a pulped material in aqueous suspension at a consistency selected in the range from about 3% to about 35% by weight, preferably from about 10% to about 30% by weight, with oxygen or an oxygen-containing gas at a partial pressure of oxygen of from about 30 to about 250 pounds per square inch gauge (psig) and at a temperature in the range from about 70° C. to about 170° C., preferably from about 100° C. to about 150° C., more preferably from about 110° C. to about 130° C., for a period of from about 10 to about 90 minutes, preferably from about 20 to about 60 minutes.

The oxygen-containing gas employed in the process commonly will be air. The use of air requires higher pressures to be used than with oxygen. For example, air will be used at 150 to 250 psig, whereas oxygen is effective at pressures of 30 to 150 psig. Also, oxygen gas may be allowed to form in situ. Oxygen may be supplied by the decomposition of hydrogen peroxide, and activators such as nitrogen dioxide can be employed in the oxygen treatment.

The treatment with oxygen or an oxygen-containing gas is carried out in the presence of 1% to 20% by weight (based on said material) of an alkali or alkaline earth base. Preferably, the base is sodium hydroxide and used in an amount in the range 1% to 10% by weight.

A viscosity preservative such as magnesium ion in an amount in the range 0.05% to 1.0% by weight may be added to the treatment with oxygen as defined hereinbefore. Suitable magnesium-containing compounds include magnesium sulphate, magnesium oxide, magnesium carbonate, and magnesium hydroxide. Other suitable additives to preserve viscosity may comprise complexing agents such as aminoalkylphosphonates and polyaminopolycarboxylates.

The treatment of the lignocellulosic material with substantially cellulase-free xylanase is performed at a consistency of 1% to 20% by weight, preferably, 2% to 12%, at a concentration of xylanase in the range 1 to 500 IU/ml at a temperature in the range 20° C. to 80° C. for a period of 1 to 48 hours. Preferably the temperature is about 50° C. Further, the treatment is carried out in an aqueous medium at pH from about 4 to about 8. The medium is optionally buffered to control the pH. Suitable buffers include but are not limited to acetate buffer and acetate/citrate buffer.

In the process according to the present invention, the xylanase is characterised as being substantially cellulase-free. By the term "substantially cellulase-free" is meant that there is not sufficient cellulase present to effect unfavourable hydrolysis of glucosidic linkages. This hydrolysis would be detrimental and unwanted in the treatment of lignocellulosic material for the purpose of improving the properties of said material in accordance with the process of the present invention herein defined. The amount of cellulase that may be tolerated depends on the particular objective in the practise of this invention.

In one feature of the process according to present invention, the oxygen treatment and the xylanase treatment as described hereinbefore are accompanied by one or more additional treatments selected from the group consisting of (i) treatment in aqueous medium with chlorine, chlorine dioxide or mixtures thereof, (ii) treatment in aqueous medium with chlorine dioxide, (iii) treatment in aqueous alkaline medium with a peroxide, (iv) treatment in aqueous medium with hypochlorite, (v) treatment in aqueous medium with ozone, (vi) treatment in aqueous medium with nitrogen dioxide.

Said one or more additional treatments may precede the oxygen and the xylanase treatments, or may be employed as intervening treatments between the oxygen and the xylanase treatments, or may follow the oxygen and the xylanase treatments, or may be employed at a combination of these alternative timings.

Preferably, in the process according to the present invention, said one or more additional treatments follow the oxygen and the xylanase treatments.

In a further feature of the process according to the present invention, said process further comprises treating said bleached lignocellulosic material resulting from at least the oxygen and the xylanase treatments as described hereinbefore with an additional treatment selected from the group consisting of (i) extraction in aqueous medium with alkali base, and (ii) oxidative extraction in aqueous medium with alkali base.

It is preferred that the oxygen and the xylanase treatments are followed by additional treatments comprising in sequence (i) treatment in aqueous medium with chlorine, chlorine dioxide or mixtures thereof, (ii) extraction or oxidative extraction in aqueous medium with alkali base, and (iii) treatment in aqueous medium with chlorine dioxide.

In a further preferred embodiment, the oxygen and the xylanase treatments are followed by additional treatments comprising in sequence (i) treatment in aqueous medium with chlorine dioxide, and (ii) treatment in aqueous alkaline medium with hydrogen peroxide.

It will be understood that in the process according to this preferred embodiment of the present invention, as well as in the process according those features and preferred embodiments described hereinbefore, the xylanase treatment may precede the oxygen treatment unless indicated otherwise.

In a further aspect, the present invention provides a bleached lignocellulosic material produced by the processes as hereinbefore defined.

In the practice of the process of the present invention the additional treatments are known in the art of pulp bleaching, both individually and in many instances in sequence, and can be carried out in any reasonable manner as is conventionally practised or known in the art. Preferred processes of the present invention for the production of bleached pulp include the sequences defined by O-X-C/D-E-D, wherein C/D denotes chlorine, chlorine dioxide, or mixtures thereof, and the extraction stage (E) is optionally an oxidative extraction as defined hereinbefore. Alternatively, the process may be defined by the sequence O-X-D-P, wherein no elemental chlorine treatment is included. By the nature of the manufacture of chlorine dioxide, there is most frequently chlorine present, which need not be removed, and is not detrimental to the process of the present invention.

The xylanase of use in the practise of the present invention is substantially cellulase-free and is obtained by the fermentation of any suitable xylanase-producing microorganism such as a xylanase-producing bacterium. The microorganism may be a naturally occurring strain, or a mutant thereof, or a strain produced by genetic engineering, i.e. a recombinant strain, to increase the production of the xylanase and/or to produce a more pure xylanase mixture, e.g., substantially cellulase-free.

Preferably, the xylanase is obtained substantially cellulase-free from a microorganism of the species *Escherichia coli, Bacillus subtilis* or of the genus Streptomyces, said microorganism having been genetically engineered to exhibit substantial cellulase negative activity. More preferably, the xylanase is obtained substantially cellulase-free from a recombinant xylanase gene-containing microorganism of the species *Streptomyces lividans*, as described by Mondue et al. (Gene, Vol. 49(3), p. 323-329, 1987).

For example, U.S. patent application Ser. No. 164,472, filed Mar. 4, 1988 (which corresponds to Canadian Patent Application Serial No. 566,839, filed May 16, 1988) describes the preparation of a genetically engineered recombinant microorganism of the genus Streptomyces and the production of substantially cellulase-free xylanase therefrom that is suitable for use in the present invention. The recombinant microorganism may be obtained by the introduction of a hybrid plasmid into a host microorganism mutant strain of the genus Streptomyces, said strain characterised by it having cellulase-negative activity, said hybrid plasmid being constructed by the insertion of a xylanase gene into a suitable vector plasmid. The hybrid plasmid is capable of inducing the extracellular secretion of cellulase-free xylanase in a host microorganism into which said plasmid has been introduced. The hybrid plasmid can be constructed by any conventional methods, such as ligation, for the insertion of the required DNA fragment, the xylanase gene, into a vector plasmid. The xylanase gene may be obtained from known strain *Streptomyces lividans* 1326. A suitable vector plasmid is the known pIJ702, which may be obtained from *Streptomyces lividans* 3131.

The hybrid plasmid may be introduced into the host microorganism by the techniques of protoplast fusion or transduction or transformation.

In the fermentation of the xylanase-producing microorganisms a source of carbon is required in the culture medium that can affect the rate of production of xylanase. For example, in the production of substantially cellulase-free xylanase by the fermentation of a recombinant microorganism of the species *Streptomyces lividans*, the medium for use in the fermentation may contain hay, wheat straw, corn stover, xylan and/or brewer's spent grains as main carbon sources, together with suitable surfactants such as olive oil and/or Tween 80 (trade mark), as described by Kluepfel et al. in Proceedings Of The 6th Canadian Bioenergy R&D Seminar, Vancouver, Canada (1987).

Where an enzyme mixture containing xylanase also contains substantial amounts of cellulase, the cellulase is removed by any method known for the purification of xylanase, or the cellulase is selectively rendered inactive by any acceptable chemical or mechanical treatment.

The xylanase may be applied as it is produced in a fermentation broth, or a concentrated mixture thereof, or as a mixture prepared from either a more concentrated mixture of the xylanase or a dried preparation of xylanase.

The xylanase treatment of lignocellulosic material according to the present invention is carried out with or without agitation. At the end of the time period for said xylanase treatment, the resultant treated material may be used directly or thickened, and said treated material then used for further processing. Optionally, a wash is included.

In a further feature of the process of the present invention, a filtrate containing residual active xylanase from the thickening and/or washing following the xylanase treatment is preferably recycled by applying said filtrate to the material to be treated with xylanase.

The process of the invention provides a bleached product having satisfactory brightness and viscosity that is equivalent to or better than that observed for pulps bleached to the same extent by conventional methods. Also, higher brightness levels can be practically achieved using the process described herein, insofar as these brightness levels could only be achieved at the expense of significantly higher chlorine-containing chemical usage and/or detrimental loss of viscosity.

The process described herein provides a bleached pulp using lower amounts of chlorine-containing compounds, and the opportunity of essentially eliminating the use of elemental chlorine, thereby reducing the polluting effluent from a pulp mill employing the process.

The process according to the present invention provides the opportunity to recycle more organic material that is removed from the starting lignocellulosic raw material to a recovery process of a mill and thus reduce the pollution load of the bleaching process.

In this specification all proportions and percentages are by weight of oven-dried material, unless otherwise stated.

The tests characterising the treated material of this invention were carried out by the following Standard Methods.

| | |
|---|---|
| Kappa Number | TAPPI Method T-236 M-76 |
| Viscosity | TAPPI Method T-230 om-82 |
| Brightness | TAPPI Method T-452 om-83 |

The invention is illustrated additionally by the following Examples but its scope is not limited to the embodiments shown therein.

EXAMPLE 1

The following example of a C/D-E-D-E-D sequence is provided for the purpose of comparison with sequences according to the present invention.

150 grams, oven-dried basis, of an unbleached hardwood kraft pulp of Kappa Number 14.1, viscosity 49.1 mPa.s and brightness 34.3% ISO was bleached by a conventional C/D-E-D-E-D bleaching sequence. The chemical charges were as follows:

C/D stage: 2.81% chlorine, 0.12% chlorine dioxide at 50° C. for 30 minutes on pulp at 3.0% consistency.
$E_1$ stage: 1.56% sodium hydroxide at 70° C. for 60 minutes on pulp at 10% consistency.
$D_1$ stage: 0.8% chlorine dioxide, 0.45% sodium hydroxide at 70° C. for 3 hours at 6.0% consistency.
$E_2$ stage: 0.4% sodium hydroxide at 70° C. for 60 minutes on pulp at 10% consistency.
$D_2$ stage: 0.1% chlorine dioxide at 70° C. for 3 hours on pulp at 6.0% consistency.

The pulp after the final chlorine dioxide stage had the following properties:

| | |
|---|---|
| Brightness | 90.0% ISO |
| Viscosity | 31.9 mPa · s |

EXAMPLE 2

The following example of an O-C/D-E-D sequence is provided for the purpose of comparison with sequences according to the present invention.

150 grams, oven-dried basis, of an unbleached hardwood kraft pulp of Kappa Number 14.1, viscosity 49.1 mPa.s and brightness 34.3% ISO were combined with 2.5% sodium hydroxide and sufficient water to give a consistency of 10% while stirring in a Hobart mixer. The pulp was then transferred to a medium consistency oxygen reactor. In the reactor the pulp was treated with oxygen-gas at a pressure of 60 pounds per square inch gauge at a temperature of 100° C. for a period of 60 minutes. The pulp was found to have a final pH of 11.4. After dilution to 4% consistency, the pulp was filtered, washed with water at 1% consistency and filtered again. The washed pulp had the following properties:

| Kappa Number | 8.3 (41% lower than unbleached) |
|---|---|
| Viscosity | 25.6 mPa · s |
| Brightness | 50.1% ISO |

The oxygen-treated pulp was then further bleached by the C/D-E-D sequence, the chemical charges and conditions being as follows:
C/D stage: 1.65% chlorine, 0.07% chlorine dioxide at 50° C. for 30 minutes on pulp at 3.0% consistency.
E stage: 0.82% sodium hydroxide at 70° C. for 60 minutes on pulp at 10% consistency.
D stage: 0.25% chlorine dioxide, 0.05% sodium hydroxide at 70° C. for 3 hours on pulp at 6.0% consistency.

The pulp bleached by the O-C/D-E-D sequence had the following properties:

| Brightness | 89.9% ISO |
|---|---|
| Viscosity | 18.9 mPa · s |

EXAMPLE 3

The following example of an X-C/D-E-D sequence is provided for the purpose of comparison with sequences according to the present invention. The xylanase treatment step will be designated by "X" in the sequences.

50 grams of the unbleached hardwood kraft pulp of Example 1, Kappa Number 14.1, viscosity 49.1 mPa.s and brightness 34.3% ISO, was treated with cellulase-free xylanase obtained from a recombinant microorganism of the species *Streptomyces lividans*. The treatment was carried out at 3% pulp consistency at 50° C. for 16 hours with agitation at 250 rpm in buffered aqueous 0.1M sodium acetate solution, pH 5, and a concentration of xylanase of 150 IU/ml. Following the enzyme treatment, the pulp was filtered, washed at 1% consistency and filtered again. The washed pulp had the following properties:

| Kappa Number | 10.8 (23% lower than unbleached) |
|---|---|
| Viscosity | 53.5 mPa · s |
| Brightness | 40.1% ISO |

The xylanase-treated pulp was then further bleached by the C/D-E-D sequence. The chemical charges and conditions were as follows:
C/D stage: 2.14% chlorine, 0.09% chlorine dioxide at 50° C. for 30 minutes on pulp at 3.0% consistency.
E stage: 1.2% sodium hydroxide at 70° C. for 60 minutes on pulp at 10% consistency.
D stage: 1.0% chlorine dioxide at 70° C. for 3 hours on pulp at 6.0% consistency.

The pulp bleached by the X-C/D-E-D sequence had the following properties:

| Brightness | 90.8% ISO |
|---|---|
| Viscosity | 30.3 mPa · s |

EXAMPLE 4

The following example is provided for comparison purposes only.

The unbleached hardwood kraft pulp of Example 2 was subjected to an oxygen treatment as in Example 2. The oxygen-treated pulp was then treated under the conditions of the xylanase treatment as outlined in Example 3 except that no xylanase was present. The pulp was then filtered, washed with water at 1% consistency and filtered. The washed pulp had the following properties:

| Kappa Number | 8.0 |
|---|---|
| Viscosity | 25.6 mPa · s |
| Brightness | 52.5% ISO |

Thus it can be seen that the oxygen-buffer sequentially treated pulp has the same Kappa Number and viscosity characteristics as the oxygen-treated pulp of Example 2. The buffer treatment has essentially no effect on these pulp properties.

EXAMPLE 5

The following is an example of an O-X-C/D-E-D sequence.

The unbleached hardwood kraft pulp of Example 2 was subjected to an oxygen treatment as in Example 2. The oxygen-treated pulp was then subjected to a xylanase treatment as in Example 3. After washing, the oxygen-xylanase-treated pulp had the following properties:

| Kappa Number | 5.3 (62% lower than unbleached) |
|---|---|
| Viscosity | 26.6 mPa · s |
| Brightness | 55.9% ISO |

The oxygen-xylanase-treated pulp was then further bleached by the C/D-E-D sequence. The chemical charges and conditions were as follows:
C/D stage: 1.05% chlorine, 0.044% chlorine dioxide at 50° C. for 30 minutes on pulp at 3.0% consistency.
E stage: 0.59% sodium hydroxide at 70° C. for 60 minutes on pulp at 10% consistency
D stage: 0.1% chlorine dioxide, 0.05% sodium hydroxide at 70° C. for 3 hours on pulp at 6.0% consistency.

The pulp bleached by the O-X-C/D-E-D had the following properties:

| Brightness | 90.5% ISO |
|---|---|
| Viscosity | 25.7 mPa · s |

The Kappa Number listed for the oxygen treatment alone in Example 2 is 8.3, which is a 41% lowering from the unbleached Kappa Number. The Kappa Number listed for the xylanase treatment alone in Example 3 is 10.8, which is a 23% lowering from the unbleached Kappa Number. By comparison, the sequential oxygen-xylanase treatment of Example 5 provided a pulp of Kappa Number 5.3, which is a 62% lowering from the unbleached Kappa Number and convincingly demonstrates a synergistic effect between the two treatments based on their individual performances, which if taken as simply additive would have been expected to yield a Kappa Number of 6.4, which corresponds to a 55% lowering.

Also, the C/D stage, E stage, and D stage chemical charges are each significantly decreased upon subsequent bleaching of the O-X treated pulp as shown in Example 5 for an O-X-C/D-E-D sequence, as compared to those chemical charges required for bleaching to a comparable or even lower final brightness in any one of the sequences C/D-E-D-E-D, O-C/D-E-D or X-C/C-E-D as illustrated by Examples 1, 2 or 3, respectively.

EXAMPLE 6

The following is an example of an X-O-C/D-E-D sequence.

The unbleached hardwood kraft pulp of Example 2 was subjected to a xylanase treatment as in Example 3, followed by an oxygen treatment as in Example 2. The X-O bleached pulp had the following properties:

| | |
|---|---|
| Kappa Number | 5.3 (62% lower than unbleached) |
| Viscosity | 30.2 mPa · s |
| Brightness | 62.3% ISO |

The X-O treated pulp was then further bleached by the C/D-E-D sequence. The chemical charges and conditions were as follows:
C/D stage: 1.05% chlorine, 0.044% chlorine dioxide at 50° C. for 30 minutes on pulp at 3.0% consistency.
E stage: 0.64% sodium hydroxide at 70° C. for 60 minutes on pulp at 10% consistency.
D stage: 0.15% chlorine dioxide at 70° C. for 3 hours on pulp at 6% consistency.

The pulp bleached by the X-O-C/D-E-D sequence had the following properties:

| | |
|---|---|
| Brightness | 91.6% ISO |
| Viscosity | 21.8 mPa · s |

The Kappa Number listed for the X-O treated pulp in this Example 6 is the same as that obtained for the O-X treated pulp in Example 5 and illustrates that the synergistic effect between the two treatments exists regardless of the order of said treatments. Also, an improved brightness and greatly improved viscosity are obtained for this X-O treated pulp as compared to the O-X treatment or O treatment alone.

The final brightness obtained in this X-O-C/D-E-D sequence is 91.6% ISO, which illustrates the effective raising of the brightness ceiling of the pulp using decreased amounts of chlorine and chlorine-containing bleaching chemicals and without introducing undesirable side effects.

EXAMPLE 7

The following is an example of an O-X-D-E-D sequence.

The unbleached hardwood kraft pulp of Example 2 was subjected to an oxygen treatment as in Example 2. The oxygen-treated pulp was then subjected to a xylanase treatment as in Example 3. The resulting pulp had the following properties:

| | |
|---|---|
| Kappa Number | 4.6 (67% lower than unbleached) |
| Viscosity | 24.1 mPa · s |
| Brightness | 60.8% ISO |

The oxygen-xylanase-treated pulp was further bleached by the D-E-D sequence, the chemical charges and conditions were as follows:
$D_1$ stage: 0.5% chlorine dioxide, 0.25% sodium hydroxide at 70° C. for 3 hours on pulp at 6.0% consistency.
E stage: 0.3% sodium hydroxide at 70° C. for 60 minutes on pulp at 10% consistency.
$D_2$ stage: 0.1% chlorine dioxide at 70° C. for 3 hours on pulp at 6.0% consistency.

The pulp bleached by the O-X-D-E-D sequence had the following properties:

| | |
|---|---|
| Brightness | 90.3% ISO |
| Viscosity | 22.4 mPa · s |

Again, this Example 7 demonstrates the synergistic effect between the oxygen and xylanase treatments, whereby a 67% lowering of the unbleached Kappa Number is obtained in this instance. Also, an improved brightness is obtained with good viscosity after the O-X treatment.

The process of the present invention as illustrated by Example 7 provides the opportunity for obtaining a high brightness fully bleached pulp using no elemental chlorine and maintaining good viscosity with, what would be considered by one skilled in the art as, relatively low chlorine dioxide charges.

EXAMPLE 8

The following is an example of an O-X-D-P sequence.

The unbleached hardwood kraft pulp of Example 2 was subjected to an oxygen treatment as in Example 2 followed by a xylanase treatment as in Example 3. The O-X bleached pulp had the following properties:

| | |
|---|---|
| Kappa Number | 4.6 (67% lower than unbleached) |
| Viscosity | 24.1 mPa · s |
| Brightness | 60.8% ISO |

The O-X bleached pulp was then further bleached by the D-P sequence, the chemical charges and conditions were as follows:
D stage: 1.0% chlorine dioxide, 0.2% sodium hydroxide at 70° C. for 3 hours on pulp at 6.0% consistency.
P stage: 0.1% hydrogen peroxide, 0.25% sodium hydroxide at 70° C. for 60 minutes on pulp at 10% consistency.

The pulp bleached by the O-X-D-P sequence had the following properties:

| | |
|---|---|
| Brightness | 90.9% ISO |
| Viscosity | 20.3 mPa · s |

In this instance, a high brightness fully bleached pulp was obtained using only four treatment steps, and again no elemental chlorine.

EXAMPLE 9

The unbleached hardwood kraft pulp of Example 2 was subjected to a sequential O-X-C/D-E-D treatment as outlined in Example 5 except that the final D stage chemical charges were 0.5% chlorine dioxide, 0.1% sodium hydroxide on pulp. The O-X-C/D-E-D bleached pulp had the following properties:

| Brightness | 91.7% ISO |
|---|---|
| Viscosity | 25.1 mPa · s |

Example 9 further demonstrates the advantages outlined at Example 5 for the process of the present invention. In particular, in this instance, is the very high brightness obtained (91.7% ISO) at a good viscosity level (25.1 mPa.s).

EXAMPLE 10

The unbleached hardwood kraft pulp of Example 2 was subjected to a sequential X-O-C/D-E-D treatment as outlined in Example 6 except that a final D stage charge of 0.08% chlorine dioxide on pulp was applied. The X-O-C/D-E-D bleached pulp had the following properties:

| Brightness | 89.1% ISO |
|---|---|
| Viscosity | 21.2 mPa · s |

Example 10 further demonstrates the advantages outlined at Example 6 for the process of the present invention.

The washing step following the xylanase treatment as is described in Example 3 hereinbefore is considered optional, but generally it is recommended that for prolonged storage of the enzyme-treated pulp, the wash be included, and the enzyme be denatured.

The embodiments of the invention in which an exclusive property or privilege is claimed are defined as follows:

1. A process for the bleaching of lignocellulosic material, derived from a chemical pulp, and having xylanase hydrolyzable xylosidic linkages, said process comprising treating, in series, said lignocellulosic material with
   (a) a sufficient amount of oxygen or an oxygen-containing gas in an oxygen treatment conducted in an alkaline medium to effect delignification and/or bleaching of said material, and
   (b) a sufficient amount of substantially cellulase-free xylanase in a xylanase treatment to effect the hydrolysis of said hydrolyzable xylosidic linkages in said material;
   to provide a bleached lignocellulosic material.

2. A process as claimed in claim 1, wherein said treatment with xylanase precedes said treatment with oxygen or an oxygen-containing gas.

3. A process as claimed in claim 1, wherein said treatment with oxygen or an oxygen-containing gas precedes said treatment with xylanase.

4. A process as claimed in claim 1, wherein said lignocellulosic material has a consistency selected from the range of from about 3% to about 35% by weight and is treated with oxygen or an oxygen-containing gas in an alkaline medium at a partial pressure of oxygen of from about 30 to about 250 pounds per square inch gauge at a temperature in the range from about 70° C. to about 170° C. for a period of from about 10 to 90 minutes.

5. A process as claimed in claim 4, wherein said lignocellulosic material has a consistency selected from the range of from about 10% to about 30% by weight and is treated with oxygen in an alkaline medium at a partial pressure of oxygen of from about 40 to about 150 pounds per square inch gauge at a temperature in the range from about 100° C. to about 130° C. for a period of from about 20 to 60 minutes.

6. A process as claimed in claim 4, wherein said lignocellulosic material is treated with oxygen or an oxygen-containing gas in the presence of from about 1 to about 20% by weight of a base of an alkali or an alkali earth metal.

7. A process as claimed in claim 4, wherein said alkali base is sodium hydroxide.

8. A process as claimed in claim 4, wherein said lignocellulosic material is treated with oxygen or an oxygen-containing gas in the presence of 0.05% to 1.0%, by weight, of magnesium ion.

9. A process as claimed in claim 1, wherein said lignocellulosic material has a consistency selected from the range of from about 1% to about 20% by weight and is treated with xylanase at a concentration of xylanase in the range 1 to 500 IU/ml at a temperature in the range 20° C. to 80° C. for a period of 1 to 48 hours.

10. A process as claimed in claim 1, wherein said treatments define therein upon said lignocellulosic material are accompanied by one or more additional treatments selected from the group consisting of
    (i) treatment in aqueous medium with chlorine, chlorine dioxide or mixtures thereof,
    (ii) treatment in aqueous medium with chlorine dioxide,
    (iii) treatment in aqueous alkaline medium with a peroxide,
    (iv) treatment in aqueous medium with hypochlorite,
    (v) treatment in aqueous medium with ozone, and
    (vi) treatment in aqueous medium with nitrogen dioxide.

11. A process as claimed in claim 1, wherein said oxygen and xylanase treatments are followed by one or more additional treatments selected from the group consisting of:
    (i) treatment in aqueous medium with chlorine, chlorine dioxide of mixtures thereof;
    (ii) treatment in aqueous medium with chlorine dioxide;
    (iii) treatment in aqueous alkaline medium with a peroxide;
    (iv) treatment in aqueous medium with hypochlorite;
    (v) treatment in aqueous medium with ozone; and
    (vi) treatment in aqueous medium with nitrogen dioxide.

12. A process as claimed in claim 1 or claim 10, said process further comprising treating said bleached lignocellulosic material with an additional treatment selected from the group consisting of
    (i) extraction in aqueous medium with alkali base, and
    (ii) oxidative extraction in aqueous medium with alkali base.

13. a process as claimed in any one of claim 1 or 3, said process further comprising treating said bleached lignocellulosic material as define therein by additional treatments comprising in sequence
    (i) treatment in aqueous medium with chlorine, chlorine dioxide or mixtures thereof, (ii) extraction or oxidative extraction in aqueous medium with alkali base, and (iii) treatment in aqueous medium with chlorine dioxide.

14. A process as claimed in any one of claims 1 to 3, said process further comprising treating said bleached lignocellulosic material as define therein by additional treatments comprising in sequence
   (i) treatment in aqueous medium with chlorine dioxide, and
   (ii) treatment in aqueous alkaline medium with hydrogen peroxide.

15. A process as claimed in claim 1, wherein said lignocellulosic material is a hardwood chemical pulp.

16. A process as claimed in claim 1, wherein said cellulase-free xylanase is obtained from a xylanase gene-containing microorganism of the genus Streptomyces.

17. A process as claimed in any one claim 1 to 3, wherein a wash step or thickening step is added following the treatment with xylanase to provide a filtrate containing residual active xylanase that is recycled by applying said filtrate to said material to be treated with xylanase.

* * * * *